US006626536B2

(12) United States Patent
Mesplay

(10) Patent No.: US 6,626,536 B2
(45) Date of Patent: Sep. 30, 2003

(54) DEVICE AND METHOD FOR ASSISTING DEVELOPMENT OF AN INFANT'S VISUAL ACUITY AND FOR TRANSFERRING A MOTHER'S SCENT TO AN INFANTILE ENVIRONMENT

(76) Inventor: Andrea W. Mesplay, 417 Brookhaven Dr., Danville, KY (US) 40422

( * ) Notice: Subject to any disclaimer, the term of this patent is extended or adjusted under 35 U.S.C. 154(b) by 167 days.

(21) Appl. No.: 09/904,379

(22) Filed: Jul. 12, 2001

(65) Prior Publication Data

US 2003/0028168 A1 Feb. 6, 2003

(51) Int. Cl.[7] ................................................. A61B 3/00
(52) U.S. Cl. ........................ 351/203; 351/246; 351/239; 442/96
(58) Field of Search ................................. 351/203, 239, 351/246; 450/1; D21/476; 442/59, 96; 428/905

(56) References Cited

U.S. PATENT DOCUMENTS

| 3,570,139 | A | | 8/1969 | Ladd et al. |
| 4,283,011 | A | | 8/1981 | Spector |
| 4,582,492 | A | | 4/1986 | Etter et al. |
| 4,631,754 | A | | 12/1986 | Ryan |
| 4,989,285 | A | | 2/1991 | Troncone et al. |
| 5,423,711 | A | | 6/1995 | Dorland |
| 5,813,866 | A | | 9/1998 | Maeda |
| 6,112,749 | A | | 9/2000 | Hall et al. |
| 6,247,178 | B1 | * | 6/2001 | Bilda ............................. 2/69 |
| 2002/0006455 | A1 | * | 1/2002 | Levine ........................ 426/104 |

OTHER PUBLICATIONS

*Enfamil Family of Formulas*, Baby Book, © Mead Johnson & Company.

* cited by examiner

Primary Examiner—Marvin M. Lateef
Assistant Examiner—John R. Sanders
(74) Attorney, Agent, or Firm—Kenneth F. Pearce

(57) ABSTRACT

A device for assisting the development of an infant's visual acuity and for transferring the mother's scent to an infantile environment. Supple fabric contacts an area of the mother's body for absorbing a portion of the mother's scent and is thereafter transferred and attached to the infantile environment for venting the transferred scent about the infantile environment. The supple fabric is also includes a contrasted black and white pattern for assisting the development of the infant's visual acuity. A second side of the device can be supplied with a neutral color.

18 Claims, 5 Drawing Sheets

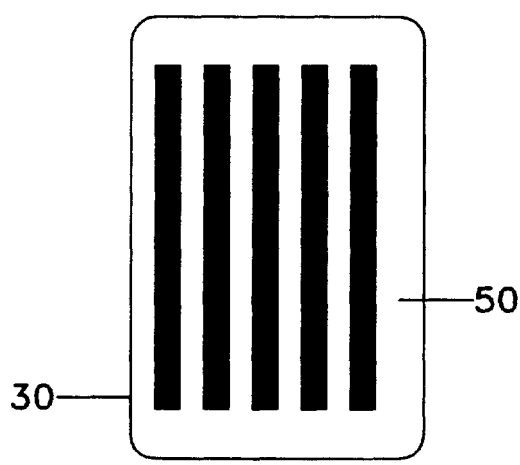
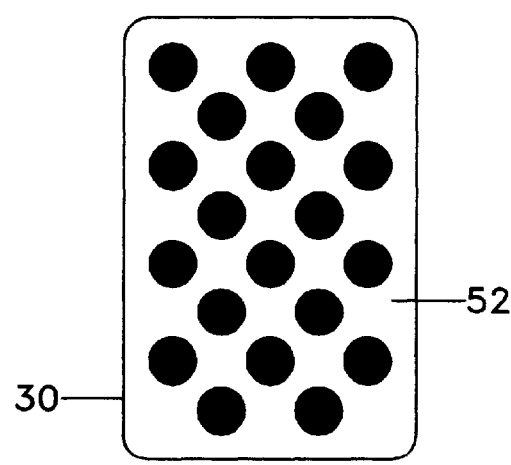
FIGURE 5          FIGURE 6
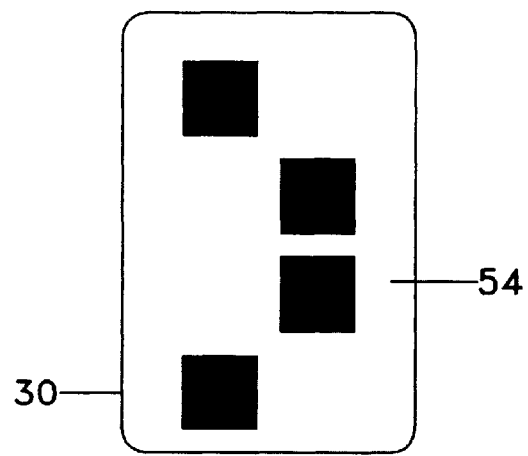
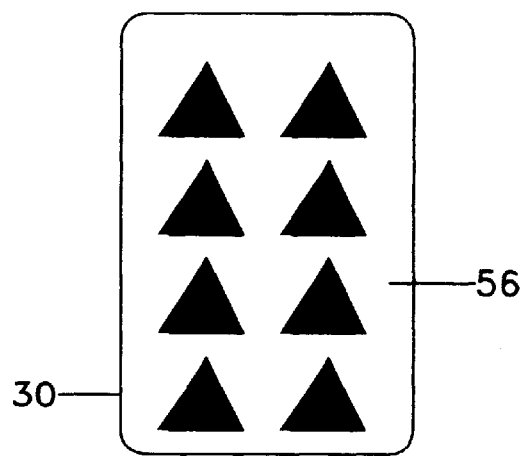
FIGURE 7          FIGURE 8

FIG 13

```
┌─────────────────────────────────────────────────────────────────────────────────┐
│ Arranging a black and white pattern about supple fabric and contrasting the black and white colors │
└─────────────────────────────────────────────────────────────────────────────────┘
                                        ⬇
                ┌──────────────────────────────────────────────┐
                │ Sizing the supple fabric to fit a cup of a brassier │
                └──────────────────────────────────────────────┘
                                        ⬇
        ┌──────────────────────────────────────────────────────────────────┐
        │ Inserting and wearing the supple fabric inside the cup of the brassier for at least four hours │
        └──────────────────────────────────────────────────────────────────┘
                                        ⬇
┌─────────────────────────────────────────────────────────────────────────────────┐
│ Removing the supple fabric from the cup of the brassier and transferring the supple fabric to the │
│                                infantile environment                            │
└─────────────────────────────────────────────────────────────────────────────────┘
                                        ⬇
┌─────────────────────────────────────────────────────────────────────────────────┐
│ Attaching the supple fabric to the infantile environment for venting the mother's scent about the │
│                         infantile environment for at least 12 hours             │
└─────────────────────────────────────────────────────────────────────────────────┘
```

DEVICE AND METHOD FOR ASSISTING DEVELOPMENT OF AN INFANT'S VISUAL ACUITY AND FOR TRANSFERRING A MOTHER'S SCENT TO AN INFANTILE ENVIRONMENT

BACKGROUND OF THE INVENTION

1. Field of the Invention

In the most general sense, the present invention relates to devices that can be attached to infantile environment, such as incubators, cradles, cribs or bassinets. The invention is especially useful in hospital wards for newborns and premature babies. Due to the highly contrasted colors about or on the device, the training of the infant's visual acuity can be enhanced. In conjunction with the highly contrasted colors, a part of the present invention is created from fabrics or other supple materials which can absorb and thereafter transfer a portion of the scent of the infant's mother to a location apart from the mother. When the device is placed near the infantile environment, the mother's scent is vented about the infant's environment. In accordance with the present invention, in the absence of the mother, the infant's olfactory senses can be stimulated by the mother's scent.

2. Description of the Previous Art a) U.S. Pat. No. 5,423,711—Dorland enables a convertible body garment with odor absorbing properties and process of using the convertible body garment. The Dorland garment is formed from a rectangular piece of fabric (16) which may be made from naturally occurring materials or blends thereof, such as cotton and/or blends with man made materials which absorb perspiration or body secretions. A pair of removable straps (18) are attached to the elongated side (20) of the rectangular shaped garment. Pockets (32) are attached to the inner surface of the garment in proximity to the breasts or axillae. The pockets are defined by a loose weave designed to retain body order absorbing material. After the mother's body odor has been absorbed, the garment (10) is attached to a crib's mattress (50). In another embodiment, the '711 garment is attached to an infant seat, carrier or swing. And Column 4, lines 23–44, teach, "In a preferred application of the invention, the use of body odor absorbing materials attached to the inner surface of the garment enhances the absorbency of odor . . . A process of promoting bonding between a person and an infant in accordance with the invention includes wearing a garment in contact with at least the person's body, such as the torso, comprising a material which absorbs odor from the body and a fastening means for attaching the garment to the body for a time sufficient to retain the odor; and attaching the worn garment to a garment support with fastening means sufficiently close to the infant so that the infant may smell the retained odor for a time sufficient to promote bonding." By reference, the disclosure of the Dorland Patent is specifically incorporated into the current Application, and more particularly, the disclosure therein related to odor absorbing materials and the resultant olfactory bonding between infants and their mothers.

2) U.S. Pat. No. 6,112,749—Hall, et. al., discloses the use of an absorbent pad made of cotton, felt, paper, etc. that has been impregnated with an odor, preferably vanilla, that is pleasing to the infant. Application of moisture activates the odor dot on the baby bottle. In another embodiment, an odor ring rather than a dot is affixed to the baby bottle. The '749 device also enables a methods inducing greater consumption of liquids, as well as, enriching the olfactory environment of the bottle's user.

3) U.S. Pat. No. 4,283,011—Spector enables a scented sticker that can be applied to clothing. The Spector stickers are embedded with a volatile having the odor analogous to the shape of the sticker.

4) U.S. Pat. No. 4,989,285—Troncone, et. al., teaches a security blanket, preferably 35 centimeters by 45 centimeters, constructed to feel like the amnion lining in which the baby resides before birth. The Troncone blanket has one side that is soft brushed flannel and a second side made of charmeuse satin.

5) U.S. Pat. No. 4,582,492—Etter, et. al., enables a behavioral modification method using microencapsulation of odors on a patch. Dominant and subservient odors are microencapsulated onto disks. When the subject's urge becomes so strong that he feels as if he is loosing control, the disk is scratched which releases the subservient odor. After a period of time, the subservient odor fades and the dominant pleasant odor becomes pervasive once again and the subject is rewarded for avoiding the bad habit.

6) U.S. Pat. No. 5,813,866—Maeda describes a bed sheet or a lap robe including a cloth chart for learning characters. A plurality of pieces and kinds of cloth in color are connected in a continuous manner along the circumference of the face of the learning chart so that beautiful feelings for infants and children are formed. Pieces (41), (42), (43), (44) and (45) are respectively red, green, yellow, brown and blue.

7) U.S. Pat. No. 3,570,139—Ladd, et. al., enables an instructional apparatus for use in early child development. The Ladd book includes visual and chemical-odor producing stimuli that allow the child to associate the thing displayed with its aroma. The display sheets (28) include incentive means (14) that are integrated with the story line as well as illustrative material to encourage the student to operate the Ladd, et. al., apparatus. For example, the '139 Patent teaches that the candy canes exemplified therein also smell like peppermint.

8) U.S. Pat. No. 5,199,842—Watt et. al., describes a nursing scarf and enables a method of nursing an infant utilizing the scarf.

9) The Enfamil® Family of Formulas™ Baby Book© 1997, Mead Johnson & Company. The Mead Johnson soft plastic Baby Book teaches, ". . . black and white patterns are easier for babies to distinguish than colors. While they can see colors, the sharp contrast of black and white holds their attention for longer periods of time." And the soft plastic Baby Book features pages of black patterns on white backgrounds.

SUMMARY OF THE INVENTION

The present device and method of using the device are directed toward assisting the developments of the infant's visual acuity and for transferring the mother's scent to an infantile environment. Infantile environments, include but are not limited to incubators, cradles, cribs or bassinets. Although select embodiments of the present invention can be practiced in home settings, it is expected that the invention will primarily be utilized in hospital settings.

Supple fabrics, such as, cottons, silks, or manmade blends that can absorb the scent of the mother are incorporated into the invention. Specifically, the supple fabrics will feel smooth to the skin, since practicing certain embodiments of the present invention require their insertion into the cup of a brassier. Those skilled in the art will recognize that the supple fabrics can also absorb the mother's scent when contacting other areas of the mother's body. However, it has been determined that insertion into the cup of the brassier provides for absorption of the mother's scent as well as ease of use.

Supple fabrics used to practice the present invention will have a breadth of no greater than 5 millimeters, preferably 1–2 millimeters, and will adequately absorb a transferable portion of the mother's scent, in minutes. Generally, the mother will wear the supple fabric inside the cup of the brassier for at least 4 hours, before attaching the device to the infantile environment where the mother's scent is to be transferred. Due to the length of time the mother will normally have the supple fabric inserted inside the cup of the brassier, it has been unexpectedly determined that the device should have a perimeter of less than 100 centimeters to prevent bulking.

According to The Enfamil® Family of Formulas™ Baby Book© 1997, Mead Johnson & Company, incorporated herein, by reference, sharply contrasted black and white colors hold an infant's attention longer. It is believed that this type of optical stimulation assists the development of the infant's visual acuity, and because of these facts, highly contrasted black and white colors are incorporated into the practice of the present invention. By way of an example, the first side of the supple fabric could be black while the second side of the supple fabric could be neutral white. In yet another exemplification, the first side of the supple fabric could include a highly contrasted black and white pattern while the second side of the supple fabric or the backing could be a neutral color, such as, white, off-white, pastel beige, pastel yellow, pastel gray, pastel blue or pastel pink.

An object of the present invention is to provide a device assisting the development of an infant's visual acuity and for transferring the mother's scent to an infantile environment.

It is another object of the present invention to enable a method for assisting the development of the infant's visual acuity and for transferring the mother's scent to the infantile environment.

Still another object of the present invention is to provide a device including highly contrasted black and white patterns for stimulating the infant's visual acuity.

Yet another object of the present invention is to provide a device including highly contrasted geometric black and white patterns for stimulating the infant's visual acuity.

Still another object of the present invention is to provide a device including highly contrasted black and white lines for stimulating the infant's visual acuity.

Yet still another object of the present invention is provide a device including a supple fabric for absorbing a portion of the mother's scent to be transferred to the infantile environment.

It is yet another object of the present invention to provide a device having a neutrally colored side or backing.

Still another object of the present invention is provide a device including a marking instrument for making a freehand impression on the neutral side of the supple fabric.

An embodiment of the present invention can be described as a device for assisting development of an infant's visual acuity and for transferring the mother's scent to an infantile environment, comprising: a supple fabric sized for insertion into a brassier worn by the mother; and a thread coupled to the supple fabric for suspending the supple fabric in the infantile environment such that said supple fabric vents the mother's scent about the infantile environment and wherein the supple fabric has a black and a neutrally contrasted side.

Another embodiment of the present invention can be described as a device for assisting development of an infant's visual acuity and for transferring the mother's scent to an infantile environment, comprising: a supple fabric sized for insertion into the brassier of the mother for absorbing the mother's scent; a black and white arrangement positioned about the supple fabric, wherein the black and white colors are contrasted; and an aperture for attaching the device to the infantile environment for venting the mother's scent.

Yet another embodiment of the present device can be described as a device for assisting development of an infant's visual acuity and for transferring a postpartum mother's scent to an infantile environment, comprising: a supple fabric sized for insertion into a brassier worn by the postpartum mother for absorbing said the postpartum mother's scent; a patterned black and white arrangement positioned about a first side of the supple fabric, wherein the black and white colors are contrasted against each other; a neutral second side of the supple fabric; and an adhesive for attaching the device to the infantile environment such that the supple fabric vents the postpartum mother's scent about the infantile environment.

In still another embodiment, the present invention can be described as a method for assisting development of infant's visual acuity and for transferring a scent of a mother to an infantile environment, comprising the steps of: arranging a black and white pattern about a supple fabric; contrasting the black and white colors against each other; sizing the supple fabric for insertion into a cup of the mother's brassier; inserting the supple fabric into a cup of the mother's brassier; wearing the supple fabric in said cup of the mother's brassier; removing the supple fabric from the cup of the mother's brassier; transferring the supple fabric to the infantile environment; and attaching the supple fabric to the infantile environment.

It is the novel and unique interaction of these simple elements which creates the methods, within the ambit of the present invention. Pursuant to Title 35 of the United States Code, descriptions of preferred embodiments follow. However, it is to be understood that the best mode descriptions do not limit the scope of the present invention.

BRIEF DESCRIPTION OF THE DRAWINGS

FIGS. 5, 6, 7, and 8 are frontal views of patterns, within the scope of the present invention.

FIG. 13 is an exemplification of the steps of yet another embodiment of the current method.

DESCRIPTION OF THE PREFERRED EMBODIMENTS

Although the disclosure hereof is detailed to enable those skilled in the art to practice the invention, the embodiments published herein merely exemplify the present invention.

Figure 1:
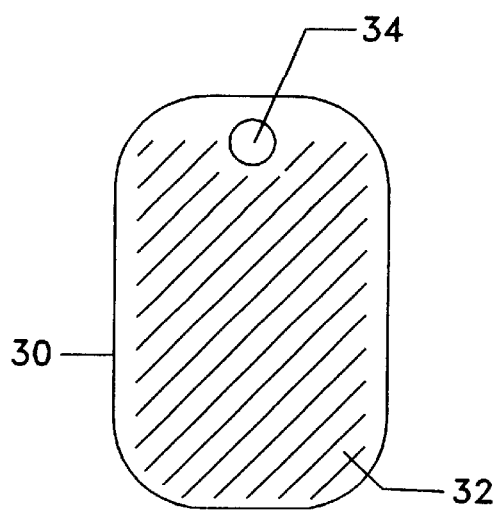
FIG. 1 is a frontal view of an embodiment, within the scope of the present invention.
Figure 2:
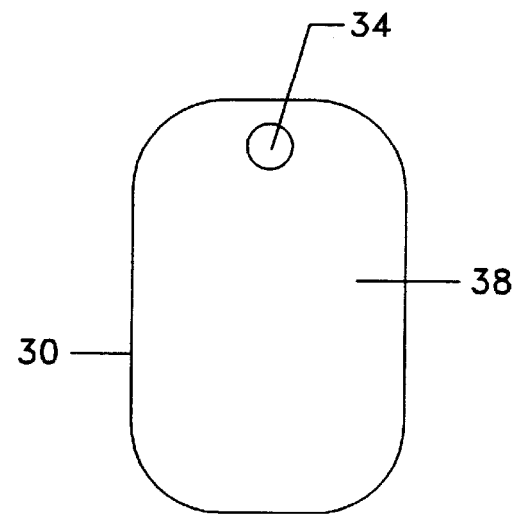
FIG. 2 is a frontal view of another embodiment, within the scope of the present invention.
Figure 3:
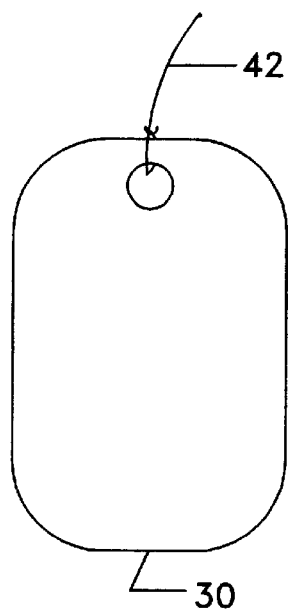
FIG. 3 is a frontal view of yet another embodiment, with the scope of the present invention.
Figure 4:
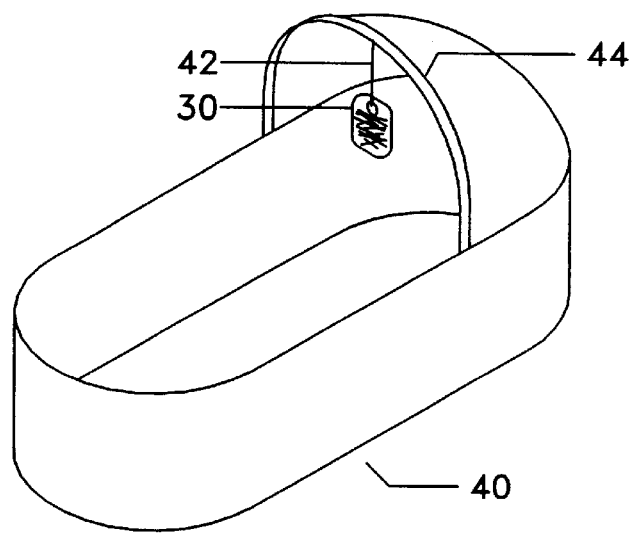
FIG. 4 is a side view of a bassinet utilizing an embodiment of the present invention.

FIG. 1 depicts a black side (32) of supple fabric (30) including an aperture (34) that can be hooked onto a projection of an infantile environment (not shown), thereby attaching supple fabric (30) to the infantile environment. FIG. 2 discloses a neutral white side (38) of supple fabric (30) and aperture (34). FIG. 3 portrays device (30) where aperture (34) has received thread (42). However, those skilled in the art recognize that thread (42) can be sewn directly into supple fabric (30), thereby circumventing use of aperture (34). FIG. 4 exemplifies, device (30) suspended from canopy (44) of bassinet (40) by thread (42).

In FIGS. 5–8, linear (FIG. 5) and other geometric black on white patterns (FIG. 6, polka dot; FIG. 7, rectangular or square; FIG. 8, triangular) are depicted. Importantly, those skilled in the art recognized the patterns could just as easily be white on black backgrounds. Moreover, practice of the present invention is not limited to patterns disclosed in FIGS. 5–8, but can easily accommodate other geometric patterns. And still in accordance with the present invention, the sides (not shown) opposite the geometric pattern sides (50, 52, 54 and 56) of supple fabric (30) are neutral, i.e., white, off-white, pastel beige, pastel yellow, pastel gray, pastel blue, pastel pink, to name a few of the plethora of neutral colors available for use. Additionally, opposite sides (not shown) can be composed of a backing separate from supple fabric (30), or it can be composed solely of supple fabric (30).

Figure 9:
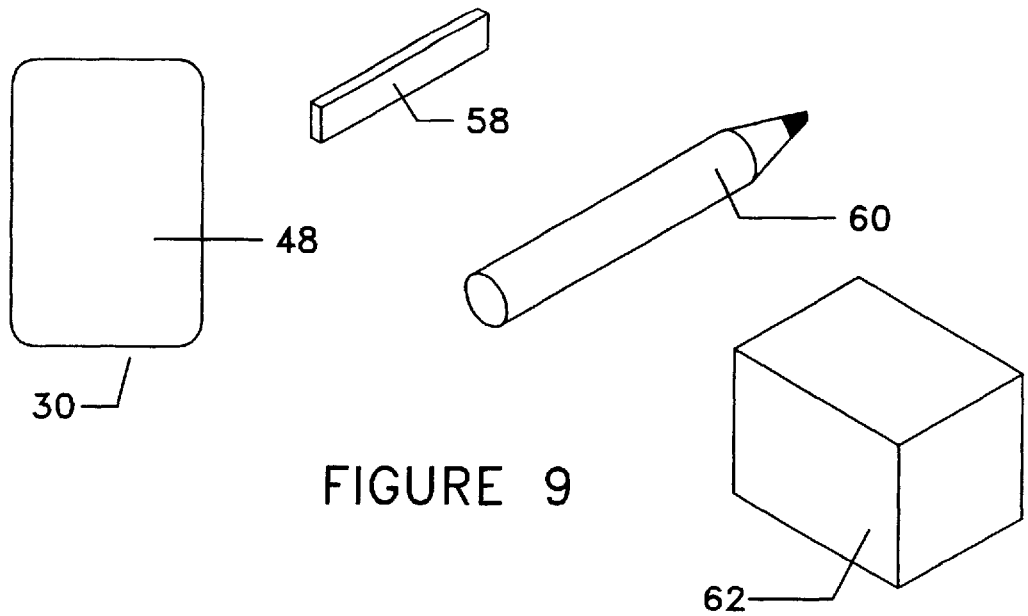
FIG. 9 is a plan view of a neutral side of an embodiment, a pictorial of marking device and a pictorial of a container, within the scope of the present invention.

Turning to FIG. 9 another embodiment of the present invention is disclosed. Neutral opposite side (48) of supple fabric or device (30) can be marked on by marking instrument (60). Any color marking instrument (60) can be included with container (62), adhesive (58) and device (30) which comprise a kit that is especially useful in hospital settings. By utilizing marking instrument (60), a freehand impression is marked on neutral side (48) of supple fabric (30) while adhesive (58) can utilized to attach device (30) to infantile environment (not shown), after the mother has worn the device for sufficient time to absorb the mother's scent. After the mother's scent has been absorbed by device (30), it is attached to the infantile environment and the mother's scent is vented about the infantile environment for stimulating the olfactory senses of the infant.

Figure 10:
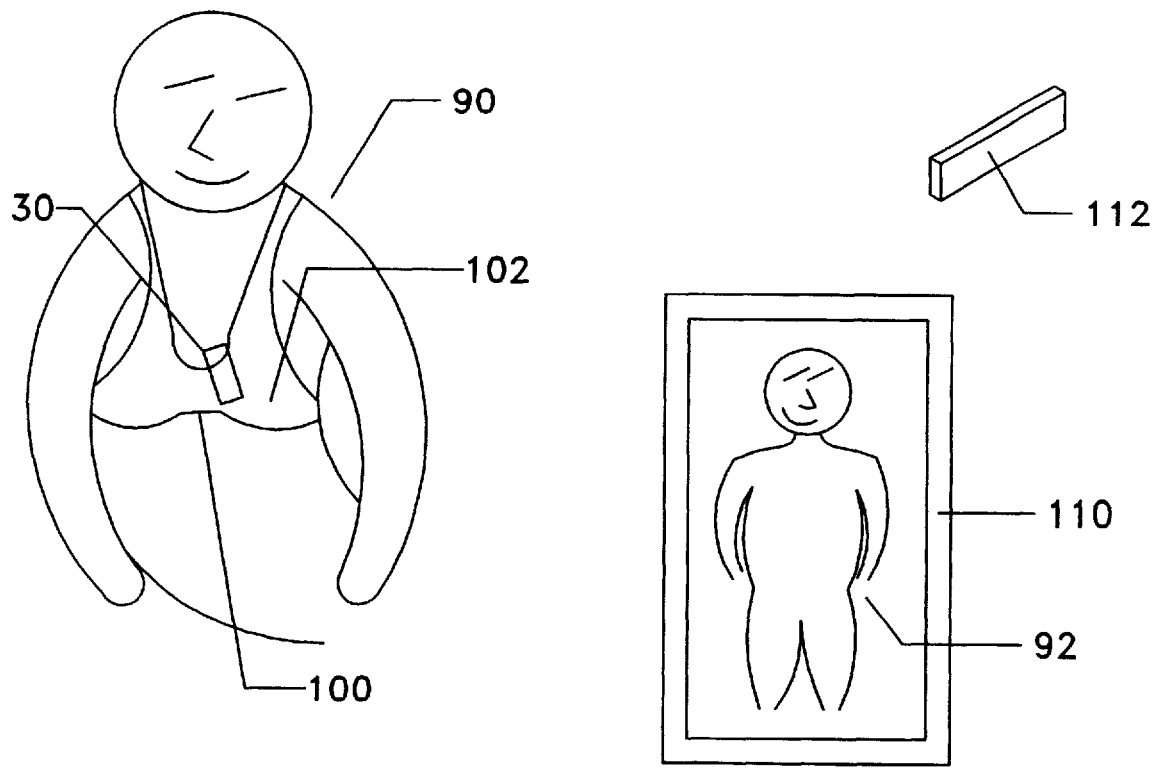
FIG. 10 is pictorial of a mother using an embodiment of the present invention and a plan view of an incubator holding an infant.

As previously disclosed, supple fabric (30) is composed of cotton, silk, or a manmade blend that will absorb a portion of the mother's scent. With a view toward FIG. 10, preferably, supple fabric (30) has a perimeter of less than 100 centimeters and a breadth of 1–2 millimeters so that it can worn comfortably inside cup (102) of brassier (100) of mother (90) for extended periods of time, if necessary. However, supple fabric (30) can also absorb a sufficient portion of the mother's scent, in minutes. Additionally, device (30) can be attached to any area of the mother's body (90) to absorb at least a portion of the mother's scent.

Figure 11:
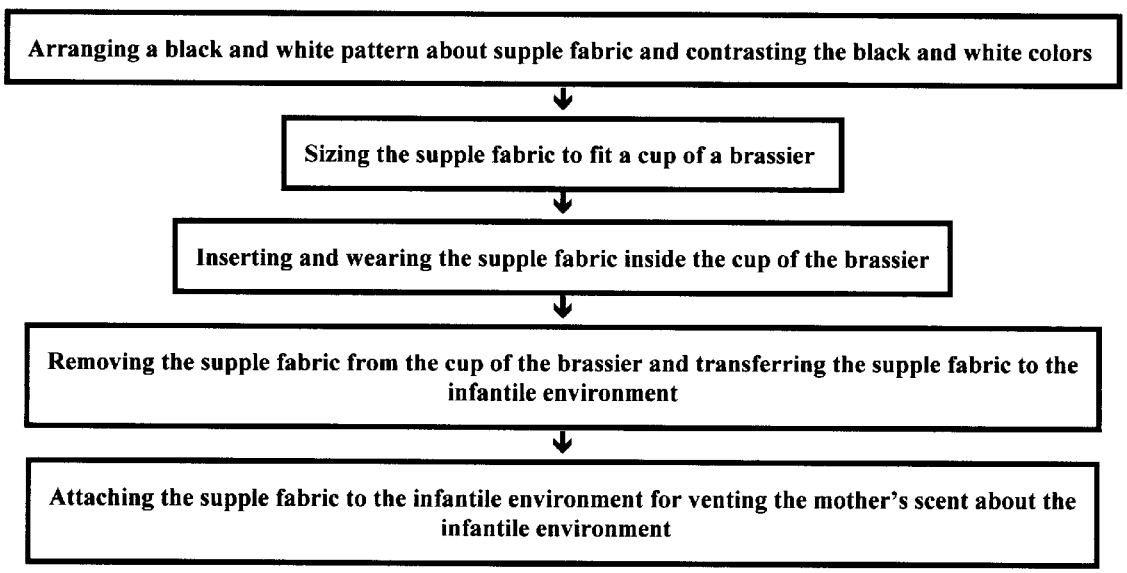
FIG. 11 is an illustration of the steps of an embodiment of the present method.
Figure 12:
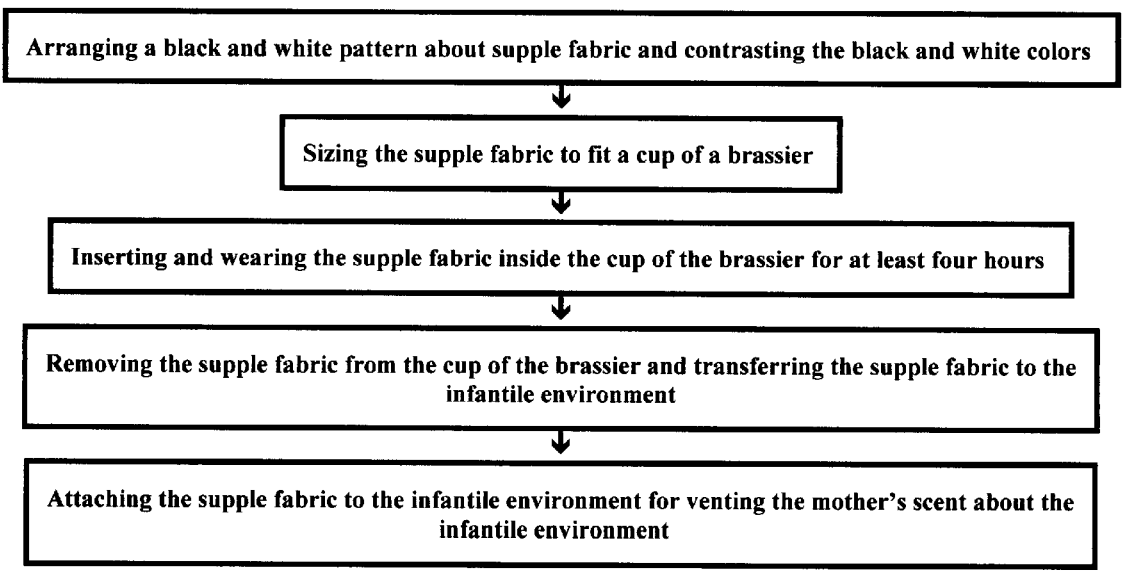
FIG. 12 is a depiction of the steps of another embodiment of the present invention.

In hospital settings, device (30) will normally be most useful for postpartum mothers and their newborns. The invention is particularly beneficial, when premature babies are required to be incubated, in hospital wards, apart from their mothers. Steps associated with the methods of practicing the present invention are depicted in FIGS. 11–13.

Returning to FIG. 10, utilization of the invention includes transferring device (30) from mother (90) for attachment to incubator (110) with adhesive (112) so that infant (92) will be exposed to device (30). In accordance with the embodiments disclosed herein, attaching device (30) to infantile environment vents the mother's scent about the infantile environment while also exposing the infant to the contrasted black and white pattern which assists in the development of the infant's visual acuity. Thus, both the infant's visual and olfactory senses are stimulated. Having disclosed the invention as required by Title 35 of the United States Code, Applicant now prays respectfully that Letters Patent be granted for her invention in accordance with the scope of the claims appended hereto.

What is claimed is:

1. A device for assisting development of an infant's visual acuity and for transferring a mother's scent to an infantile environment, comprising:
   a) supple fabric sized for insertion into a brassier worn by said mother for absorbing said mother's scent and for assisting development of said infant's visual acuity, after said supple fabric is removed from said brassier; and
   b) thread coupled to said supple fabric for suspending said supple fabric in said infantile environment such that said supple fabric vents said mother's scent about said infantile environment and wherein said supple fabric has a patterned black and white first side and a second side neutrally contrasted to said black and white first side.

2. The invention of claim 1 further comprising an eye for receiving said thread.

3. The invention of claim 2 wherein said device's perimeter is less than 100 centimeters and breadth is less than 5 millimeters.

4. A device for assisting development of an infant's visual acuity and for transferring a mother's scent to an infantile environment, comprising:
   a) a supple fabric sized for insertion into a brassier worn by said mother for absorbing said mother's scent;
   b) a black and white arrangement positioned about said supple fabric, wherein said black and white colors are contrasted against each other for assisting development of said infant's visual acuity; and
   c) an aperture for attaching said device to said infantile environment, after said supple fabric's removal from said brassier, such that said supple fabric vents said mother's scent about said infantile environment.

5. The invention of claim 4 further comprising an adhesive for attaching said device to said infantile environment.

6. The invention of claim 5 wherein said black and white arrangement is patterned.

7. The invention of claim 6 further comprising a neutral backing for said supple fabric.

8. The invention of claim 7 wherein said device's perimeter is less than 100 centimeters and breadth is less than 5 millimeters.

9. A device for assisting development of an infant's visual acuity and for transferring a postpartum mother's scent to an infantile environment, comprising:
   a) a supple fabric sized for insertion into a brassier worn by said postpartum mother for absorbing said postpartum mother's;
   b) a patterned black and white arrangement positioned about a first side of said supple fabric, wherein said black and white colors are contrasted against each other for assisting development of an infant's visual acuity;
   c) a neutral second side of said supple fabric; and
   d) an adhesive for attaching said device to said infantile environment, after said supple fabric's removal from said brassier, such that said supple fabric vents said postpartum mother's scent about said infantile environment.

10. The invention of claim 9 wherein said device's perimeter is less than 100 centimeters and breadth is less than 5 millimeters.

11. The invention of clam 10 wherein said patterned black and white arrangement is geometric.

12. The invention of claim 11 further comprising a marking instrument for making a freehand impression on said neutral second side of said supple fabric.

13. The invention of claim 12 further comprising a container for containing said device, said adhesive and said marking instrument prior to utilization of said device.

14. The invention of claim 13 wherein said freehand impression is marked in a color other than black or white.

15. A method for assisting development of infant's visual acuity and for transferring a scent of a mother to an infantile environment, comprising the steps of:

a) arranging a black and white pattern about a supple fabric;

b) contrasting said black and white colors against each other;

c) sizing said supple fabric for insertion into a cup of said mother's brassier;

d) inserting said supple fabric into a cup of said mother's brassier;

e) wearing said supple fabric in said cup of said mother's brassier;

f) removing said supple fabric from said cup of said mother's brassier;

g) transferring said supple fabric to said infantile environment; and h) attaching said supple fabric to said infantile environment.

16. The method of claim 15 wherein said step of arranging a black and white pattern about a supple fabric is a geometric arranging.

17. The invention of claim 16 wherein said step of wearing said supple fabric in said cup of said mother's brassier is for at least four hours.

18. The invention of claim 17 further comprising the step of venting said infantile environment with said scent of said mother for at least 12 hours.

\* \* \* \* \*